United States Patent [19]

Debrauwere et al.

[11] Patent Number: 5,445,629
[45] Date of Patent: Aug. 29, 1995

[54] BLOOD STORAGE CONTAINER AND METHODS OF USING SAME

[75] Inventors: Jack Debrauwere, Halle; Jean-Claude Bernes, Faimes; Jean-Marie Mathias, Lillois, all of Belgium

[73] Assignee: Baxter International Inc., Deerfield, Ill.

[21] Appl. No.: 171,084

[22] Filed: Dec. 21, 1993

[51] Int. Cl.⁶ .................. A61M 37/00; A61B 19/00
[52] U.S. Cl. .................. 604/403; 604/87; 604/408; 604/416
[58] Field of Search ........... 128/DIG. 24; 604/82, 604/87, 88, 403, 408, 411–416

[56] References Cited

U.S. PATENT DOCUMENTS

| | | |
|---|---|---|
| 3,874,348 | 4/1975 | Deindorfer et al. |
| 4,305,443 | 12/1981 | Bayham ............ 604/408 |
| 4,443,220 | 4/1984 | Hauer et al. |
| 4,902,287 | 2/1990 | Carmen et al. ........ 604/408 |
| 4,938,758 | 7/1990 | Al-Sioufi |
| 5,141,645 | 8/1992 | Shiraki et al. ........ 604/408 |
| 5,259,843 | 11/1993 | Watanabe et al. ..... 604/408 |
| 5,306,269 | 4/1994 | Lewis .............. 604/408 |

FOREIGN PATENT DOCUMENTS

0075576 9/1985 European Pat. Off.

OTHER PUBLICATIONS

WO 90/97876, pub. Jul. 26, 1990.
WO 89/04639, pub. Jun. 1, 1980.
WO 87/06229, pub. Oct. 22, 1987.
WO 83/02226, pub. Jul. 7, 1983.
WO 92/15274, pub. Sep. 17, 1992.
EP 505251 A1, pub. Mar. 28, 1992.
EP 469–515 A, pub. Jul. 29, 1991.
EP 455–215 A, pub. Apr. 30, 1991.
EP 398–321 A, pub. May 17, 1990.
EP 330–785 A, pub. Dec. 9, 1988.
EP 315–740 A, pub. Aug. 12, 1988.
EP 253–651 A, pub. Jul. 15, 1987.
EP 175–274 A, pub. Sep. 11, 1985.
EP 84–512 A, pub. Jan. 7, 1983.
EP 76–062, pub. Sep. 16, 1982.

Primary Examiner—C. Fred Rosenbaum
Assistant Examiner—Frank Wilkens, III
Attorney, Agent, or Firm—Bradford R. L. Price; Paul C. Flattery; Robert M. Barrett

[57] ABSTRACT

A container for housing body fluids. The container comprises a body defined by flexible walls having an interior for housing the body fluid. An elongated tube extends from the body for housing a fluid to be added to the body fluid. The tube includes means for allowing selective fluid flow from the interior of the tube to the interior of the body allowing the fluid to be added to the body fluid. Additionally, the means for allowing selective fluid flow allows the body fluid to be expressed from the body of the container into the elongated tube. The present invention also provides a method for storing and treating blood.

25 Claims, 1 Drawing Sheet

BLOOD STORAGE CONTAINER AND METHODS OF USING SAME

BACKGROUND OF THE INVENTION

The present invention generally relates to the storage of body fluids. More specifically, the present invention relates to the storage and use of blood and its components.

It is, of course, known to use blood and other body fluids in a number of medical procedures. Blood transfusions are an example of such procedures. Blood is collected from a donor and can be transfused into a recipient.

Blood after being received from a donor is stored, typically, in flexible plastic containers until use. Blood can either be housed and stored in a container as whole blood or broken down into its individual components, e.g., plasma, buffy coat layer, and packed red cells. For example, it is known to separate whole blood either through a centrifuge process or a process such as that disclosed in U.S. Pat. Nos. 4,350,585 and 4,608,178 into plasma, buffy coat, and packed red cells.

In a great majority of cases, blood is stored for a number of days and not immediately infused into a recipient. In most situations, the blood components are separately stored. For example, it is known to separately store and utilize the red blood cell component of whole blood.

In order to maintain the viability of red blood cells and other blood components, it is necessary to provide a storage solution. For example, the storage solution provides an energy source for the red blood cells.

Such storage solutions typically include a sugar component, such as glucose, as well as other components, such as, e.g., sodium citrate, sodium bisphosphate, sodium phosphate dibaSic, adenine, and mannitol. One of the difficulties encountered with storage solutions is during the sterilization of the solution. Glucose is known to degrade under autoclaving (heat) sterilization 10 conditions unless maintained in an acidic medium. If glucose is not in an acidic medium, when heated, glucose will caramelize.

However, it is considered as an advantage for storage solutions to be formulated at a pH as close as possible to the physiological pH of blood (pH 7.4) in order to better maintain red cells properties. Therefore, a problem that has been encountered is the sterilization of storage solutions containing dextrose and buffered at a neutral pH.

Other fluids that may be added to blood or a blood component may also raise stability and sterilization issues if provided in the container that will store the blood component. For example, as set forth in U.S. patent application Ser. No. 07/952,427 entitled: "STEAM STERILIZABLE SYSTEM FOR INACTIVATING VIRAL CONTAMINANTS IN BODY FLUIDS", methylene blue (3-7bis(dimethyl amino phenothiazine-5-ium chloride), a viral inactivation agent, may leach into certain plastics if heated.

As set forth in that patent application, if methylene blue is placed in a standard blood pack unit constructed from polyvinyl chloride (PVC) under standard conditions and the unit is then sterilized, at least a portion of the methylene blue migrates into the PVC layer reducing the methylene blue present. The specific amount of methylene blue that migrates is variable depending on conditions. However, a precise amount of methylene blue may be maintained during sterilization when it is contained in an elongated tube whose inside layer or total layer is made of a non-PVC material. Envisioned methods of using methylene blue to treat blood and other body fluids require that precise amounts of methylene blue be used. Plastics such as PVC, however, may exhibit desirable characteristics for storing blood or its components.

Of course, one of the issues in transfusing blood into a patient is insuring that the blood is compatible with the patient's blood. For example, it is known to insure that similar blood types are infused into the patient. In order to type or match the blood, it is necessary for a sample of blood to be accessed and tested so as to determine the type and other characteristics of the blood or component.

SUMMARY OF THE INVENTION

The present invention provides a container for housing body fluids. The container comprises a body defined by flexible walls having an interior for housing the body fluid. An elongated tube extends from the body for housing a fluid to be added to the body fluid. The tube includes means for allowing selective fluid flow from the interior of the tube to the interior of the body allowing the fluid to be added to the body fluid. Additionally, the means for allowing selective fluid flow allows the body fluid to be expressed from the body of the container into the elongated tube.

In a preferred embodiment, the container is designed for housing blood or a blood component.

Additionally, the present invention provides a method for storing a blood component. The method comprises the steps of providing a container having a body that defines an interior chamber. An elongated tube is coupled to the body. The tube includes an interior having a fluid therein. A frangible valve or cannula is selectively broken to allow the fluid to be added to the interior chamber of the container. Blood flows into the container through a port in the container. The blood mixes with the fluid. A portion of the blood is then expressed into the tube. The tube is severed from the remaining portions of the body. The tube then can be used for cross matching the blood to the recipient.

Additionally, the present invention provides a method for storing a blood component. The method comprises the step of providing a container having a body having an interior chamber including therein a first portion of a blood storage solution. The container also includes an elongated tube housing a second portion of a blood storage solution. The second portion of the blood storage solution is added to the first portion of the blood storage solution by breaking a frangible and causing the second portion of the blood storage solution to flow into the interior chamber of the body. Blood is then added to the interior chamber of the body. A portion of the blood is expressed into the tube. The tube is then severed from the body and can be used for cross matching.

In an embodiment, the tube is severed by heat sealing the tube.

In an embodiment, the method includes the step of sterilizing the container and tube prior to adding blood to the interior of the body.

Additionally, the present invention provides a method for inactivating pathogens that may be present in a body fluid. Pursuant to the method, a viral inactivating agent is located in the elongated tube and added to the body fluid. A portion of the body fluid is then expressed into the tube that is severed and can be used for cross matching or for any other blood component testing.

In an embodiment, the viral inactivating agent is a photoactive compound.

In an embodiment, the viral inactivating agent is selected from the group consisting of: psoralens; porphyrins; phthalocyanines; and dyes such as methylene blue.

In an embodiment, the container is irradiated with light of a suitable wavelength to activate the photoactive compound before the tube is severed from the body of the container.

An advantage of the present invention is that it provides an improved container for housing blood or a blood component.

Another advantage of the present invention is that it provides an improved method for storing a blood component.

Still further, an advantage of the present invention is that it provides an improved method for sterilizing a blood storage solution and adding same to a blood component.

Furthermore, an advantage of the present invention is that it provides an improved method for adding a viral inactivation agent to a blood component.

Moreover, the present invention provides an improved method for cross matching blood.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an apparatus and method for storing blood. As used herein, the term "blood" includes whole blood as well as its components including, but not limited to, red blood cells, plasma, platelets, and leukocytes.

Pursuant to the present invention, blood is stored in a container that has extending therefrom an elongated tube. The elongated tube includes a fluid that is added to the blood that is stored in the container. The fluid can comprise a portion of a storage solution which provides nutrients to the blood. However, the fluid can comprise other compositions that are added to blood. For example, the fluid can be a viral inactivation agent for inactivating viruses that may be present in the blood or in the blood component.

Figure 1:
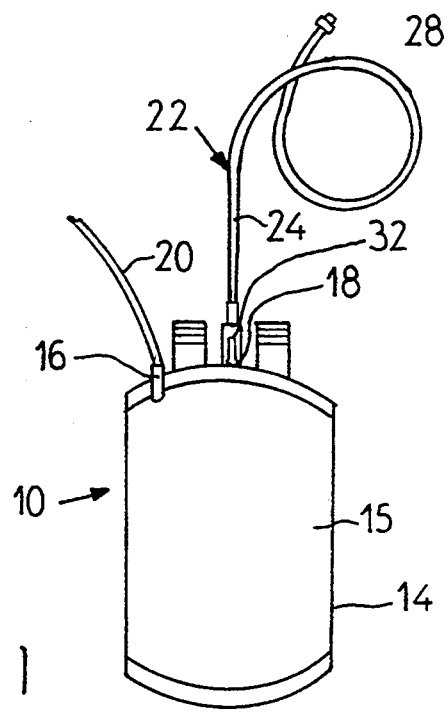
FIG. 1 illustrates a perspective view of a container of the present invention.

Referring now to the Figures, and specifically FIG. 1, in an embodiment, a container 10 is provided that comprises a body 12 constructed from preferably flexible sheets of plastic. The sheets are sealed along their edges 14 to create an interior 15. A number of plastics can be utilized. Depending on the specific components to be stored, certain plastics may be more desirable. In an embodiment, the container is constructed from a polyvinyl chloride material that is plasticized and includes stabilizers.

As illustrated, the container 10 includes a number of ports that provide access to the interior 15 of the container 10. Through one of the ports 16, blood can be infused into the container. In this regard, a fluid line 20 extends either from a donor needle or from another container including blood. Blood then flows through the tube 20 into the interior 15 of the container 10.

Pursuant to the present invention, extending from one port 18 is an elongated flexible tube 22. The elongated tube 22 defines an interior 24 for housing a fluid to either be added to the container 10 or to the blood stored in the container 10. The elongated flexible tube 22 is sealed at one end 28 by a heat seal or other means.

In the preferred embodiment illustrated, in order to provide selective fluid communication between the interior 24 of the tube 22 and the interior 15 of the container 10, a frangible cannula 32 is utilized. To provide fluid communication, the frangible cannula 32 is biased so that a portion thereof breaks away from the remaining portions of the cannula. This allows the fluid within the tube 22 to flow into the interior 15 of the container 10. Although in the embodiment illustrated a frangible cannula 32 is used, any means for allowing selective access between the interior 24 of the flexible tube 22 and the container 10 can be utilized.

The length of the tube 22 is chosen so as to provide sufficient fluid volume for the specific application to be utilized. Likewise, the fluid to be stored within the tube 22 is dependent on the application desired.

For example, reference is made to U.S. patent application Ser. No. 07/610,478 entitled: "RED BLOOD CELL STORAGE SOLUTION," the disclosure of which is hereby incorporated by reference. As set forth therein, pursuant to that invention, a method is provided for storing red blood cells comprising providing a two-part storage solution. A first distinct solution is provided including at least one sugar. In the second solution, a composition is provided comprising adenine, mannitol, sodium citrate, sodium bisphosphate, sodium phosphate dibasic, and if desired, guanosine.

Pursuant to the present invention the dextrose or sugar component can be stored in the tube 22 whereas the second distinct solution will be stored in the container 10. This allows the sugar to be stored at an acidic pH in the tube 22 and the second solution in the container 10 to be stored at a neutral pH. Therefore, the container 10 and tube 22 including the storage solution can be autoclaved without causing the dextrose to caramelize.

For example, in an embodiment, a 94 ml solution of citrate, phosphate, mannitol, and adenine is stored at a pH of approximately 7.4 in the container 10 and 6 ml of 15% dextrose is stored at a pH of approximately 5.8 in the tube 22.

When it is desired to add red blood cells to the container 10 for storage, the frangible cannula 32 is broken. The sugar solution is then expressed into the container 10 where it is mixed with the second solution. To assist in adding the fluid to the container 10 from the tube 22, a tube stripper can be used. When the sugar solution is added to the container 10, this will create 10 a red cell storage solution. The blood can then be added to the container 10.

In another embodiment, the fluid in the tube 22 is a viral inactivation agent, preferably a photoactive agent.

Either before or after the blood component has been added to the container, the viral inactivation agent can be added to the container.

A number of different photoactive agents have been proposed as possibilities to be used to eradicate viral and other contaminants in body fluids. Such photoactive agents include: psoralens; porphyrins; phthalocyanines; and dyes such as methylene blue. See, for example, U.S. Pat. Nos.: 4,748,120; 4,878,891; 5,120,649; and German Patent Application No. DE 39 30 510 A1 (Mohr).

By way of example, methylene blue can be used. The present invention is uniquely designed to meet the special concerns when methylene blue is used. In this regard, reference is made to U.S. patent application Ser. No. 07/952,427, the disclosure of which is incorporated herein by reference.

If methylene blue is used, preferably, the tube 22 is constructed from a material having at least an inner layer, that defines the interior, that is constructed from a non-PVC material. If desired, the tubing 22 can be constructed from a monolayer or a multi-layer material.

If a monolayer material is used, preferably, it is a non-PVC material. Most preferably, the monolayer material is solvent sealable to PVC, allowing the tube 22 to be sealed to a standard PVC container 10.

Figure 2:
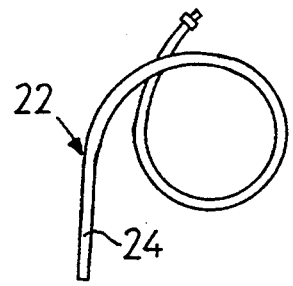
FIG. 2 illustrates the tube including the blood component to be cross matched severed from the container of FIG. 1.

Pursuant to the present invention, after the fluid within the tube 22 is added to the container 10, and after the blood has been added to the container 10, the blood can be expressed into the tube 22. As illustrated in FIG. 2, after the blood is expressed in the tube 22, the tube can be severed from the container 10. A variety of methods can be used to so sever the tube 22 including using a heat sealer. The tube 22 can then be used for cross matching purposes.

Figure 3:
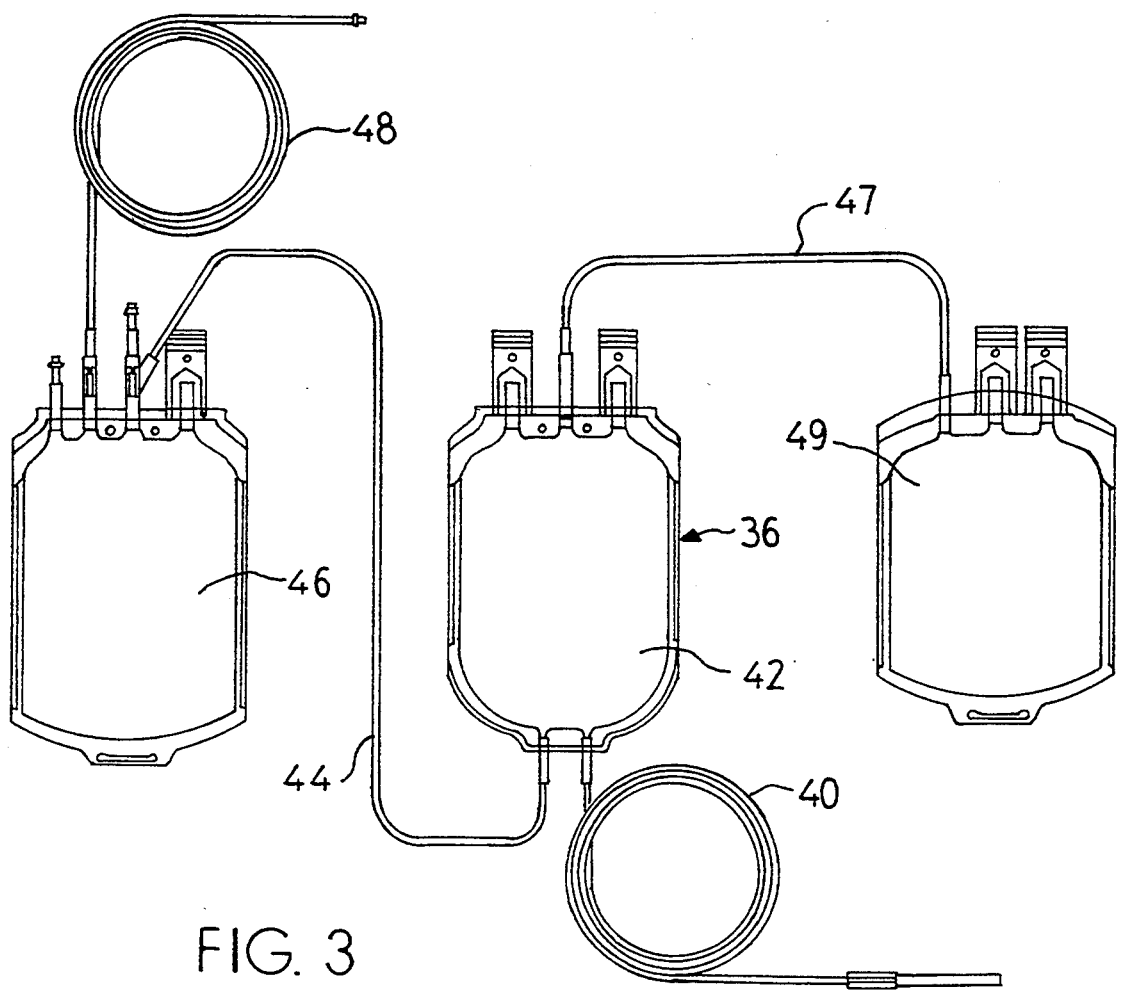
FIG. 3 illustrates an embodiment of the container of the present invention containing a blood collection and separation system.

FIG. 3 illustrates an embodiment of the invention illustrating a system 36 that can be used for receiving whole blood and separating it into plasma, red blood cells, and buffy coat using a process disclosed in U.S. Pat. Nos. 4,608,178, the disclosure of which are incorporated herein by reference. Blood is originally received through a donor tube 40 by a container 42. By using a press, the red blood cells flow through tube 44 into container 46, plasma flows through tube 47 into container 49. The container 46 includes a tube 48 that functions as set forth above and can include, e.g., a storage solution or photoactive agent.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for storing blood comprising the steps of:
   providing a container having a body, an interior chamber, means for receiving blood, an elongated tube coupled to the body, the tube including an interior having a fluid therein and means for allowing selective fluid communication between the interior of the tube and the interior chamber;
   providing fluid communication between the interior of the tube and the interior chamber;
   causing the fluid to flow into the interior of the container;
   passing the blood through the means for receiving blood into the container;
   expressing a portion of the blood into the elongated tube; and
   severing the elongated tube from the body of the container.

2. The method of claim 1 wherein the fluid is added to the container prior to adding the blood.

3. The method of claim 1 wherein the fluid includes at least one component of a blood storage solution.

4. The method of claim 1 wherein the fluid is a viral inactivation agent chosen from the group consisting of: porphyrins; psoralens; phthalocyanines; and dyes.

5. The method of claim 1 wherein the tube is severed through a heat seal.

6. The method of claim 1 wherein the tube is constructed from a different material than the container.

7. The method of claim 1 wherein to provide fluid communication, a frangible cannula is broken.

8. A method for storing blood comprising the steps of:
   providing a container having a body defining an interior chamber including a first portion of a blood storage solution, the container including an elongated houses in an interior of the tube a second portion of a blood storage solution;
   providing a frangible member to initially prevent fluid communication between the interior of the tube and the interior chamber;
   adding the second portion to the first portion by breaking the frangible and causing the second portion to flow into the interior chamber;
   adding a blood component through a tube in fluid communication with the interior chamber;
   expressing a portion of the blood into the tube; and
   severing the tube from the body.

9. The method of claim 8 wherein the tube is severed by heat sealing the tube.

10. The method of claim 8 including the step of sterilizing the container and tube prior to adding blood to the interior of the body.

11. The method of claim 8 wherein the tube is constructed from a different material than the container.

12. A method for treating blood comprising the steps of:
   providing a container having a body defining an interior chamber, the container including an elongated tube that houses a photoactive agent;
   providing a frangible member initially prevent fluid communication between the tube and the interior chamber;
   adding the photoactive agent to the interior chamber by breaking the frangible and causing the photoactive agent to flow into the interior chamber;
   adding a blood component through a port in fluid communication with the interior chamber;
   exposing the container to light of a suitable wavelength to activate the photoactive agent;
   expressing a portion of the blood into the tube; and
   severing the tube from the body.

13. The method of claim 12 wherein the tube is severed by heat sealing the tube.

14. The method of claim 12 including the step of sterilizing the container and tube prior to adding blood to the interior of the body.

15. The method of claim 12 wherein the tube is constructed from a different material than the container.

16. The method of claim 12 wherein the photoactive agent is methylene blue.

17. A method for storing a blood solution comprising the steps of:

providing a container having a body defining an interior chamber including a first portion of blood storage solution, the container including a means for adding blood to the interior chamber and an elongated tube that houses in an interior of the elongated tube a second portion of blood storage solution;

autoclaving the container and the elongated tube;

adding the second portion to the interior chamber;

adding a blood component through the means for adding blood to the interior chamber;

expressing a portion of the blood into the tube; and severing the elongated tube from the body.

18. The method of claim 17, wherein the first portion of a blood storage solution includes dextrose.

19. The method of claim 17, wherein the container and the elongated tube are autoclaved simultaneously to sterilize same.

20. The method of claim 17, wherein the first portion of a blood storage solution is stored at an acidic pH.

21. The method of claim 17, wherein the second portion of a blood storage solution is stored at a basic pH.

22. The method of claim 17, wherein the blood is added to the interior chamber before the second portion.

23. A method for cross matching blood comprising the steps of:

providing a container having a body, an interior chamber, means for receiving blood, an elongated tube coupled to the body, the tube including an interior having a fluid therein and means for allowing selective fluid communication between the interior of the tube and the interior chamber;

providing fluid communication between the interior of the tube and the interior chamber;

causing the fluid to flow into the interior of the container;

passing the blood through the means for receiving the blood into the interior of the container;

expressing a portion of the blood into the elongated tube;

severing the tube from the container; and testing blood from the tube for blood type cross matching.

24. The method of claim 23, wherein the blood is received by the interior chamber before the fluid flows into the body of the container.

25. The method of claim 24, wherein the means for receiving blood is a port.

* * * * *

UNITED STATES PATENT AND TRADEMARK OFFICE
CERTIFICATE OF CORRECTION

PATENT NO. : 5,445,629
DATED : August 29, 1995
INVENTOR(S) : Jack Debrauwere, Jean-Claude Bernes and Jean-Marie Mathias It is certified that error appears in the above-identified patent and that said Letters Patent are hereby corrected as shown below:

Column 6, line 26, in Claim 8, before "houses", insert --tube that--.

Column 6, line 50, in Claim 12, after "member", insert --to--.

Signed and Sealed this

Twenty-eighth Day of November 1995

Attest:

BRUCE LEHMAN

Attesting Officer     Commissioner of Patents and Trademarks